(12) United States Patent
Goutsis et al.

(10) Patent No.: US 10,702,459 B2
(45) Date of Patent: Jul. 7, 2020

(54) HAIR DYE HAVING IMPROVED VISCOSITY STABILITY

(71) Applicant: Henkel AG & Co. KGaA, Duesseldorf (DE)

(72) Inventors: Konstantin Goutsis, Juechen (DE); Daniela Kessler-Becker, Leverkusen (DE)

(73) Assignee: Henkel AG & Co. KGaA, Duesseldorf (DE)

( * ) Notice: Subject to any disclaimer, the term of this patent is extended or adjusted under 35 U.S.C. 154(b) by 0 days.

(21) Appl. No.: 16/134,512

(22) Filed: Sep. 18, 2018

(65) Prior Publication Data

US 2019/0083372 A1    Mar. 21, 2019

(30) Foreign Application Priority Data

Sep. 19, 2017  (DE) .................. 10 2017 216 537

(51) Int. Cl.
  *A61Q 5/10*  (2006.01)
  *A61K 8/19*  (2006.01)
  *A61K 8/23*  (2006.01)

(52) U.S. Cl.
  CPC ............... *A61K 8/19* (2013.01); *A61K 8/23* (2013.01); *A61Q 5/10* (2013.01); *A61K 2800/4324* (2013.01); *A61K 2800/88* (2013.01); *A61K 2800/882* (2013.01)

(58) Field of Classification Search
  CPC ........ A61Q 5/10; A61K 8/411; A61K 8/4926; A61K 8/415; A61K 8/22; A61K 8/19; A61K 2800/88; A61K 2800/4324; A61K 8/347; A61K 2800/882; A61K 8/46; A61K 8/466; A61K 8/06
  See application file for complete search history.

(56) References Cited

U.S. PATENT DOCUMENTS

| 5,525,123 A * | 6/1996 | Lorenz .................... A61K 8/19 8/406 |
| 5,609,650 A | 3/1997 | Knuebel et al. |
| 2013/0142748 A1* | 6/2013 | Tamura .................. A61K 8/894 424/70.12 |
| 2016/0074292 A1 | 3/2016 | Goutsis et al. |
| 2017/0172900 A1* | 6/2017 | Kerl ...................... A61Q 5/065 |

FOREIGN PATENT DOCUMENTS

| GB | 917840 A | 2/1963 |
| JP | 3936960 B1 | 6/2007 |

* cited by examiner

*Primary Examiner* — Eisa B Elhilo
(74) *Attorney, Agent, or Firm* — Lorenz & Kopf, LLP

(57) ABSTRACT

The present application relates to agents for dyeing keratin fibers, in particular human hair, exemplified in that said agents are produced by mixing
(A) one or more oxidation dye precursors in salt form and
(B) one or more water-soluble salts of barium and/or of calcium,
wherein the molar ratio of all oxidation dye precursors in salt form (A) used in the agent to all water-soluble barium and calcium salts (B) used in the agent. i.e. the molar ratio (A)/(B), lies at a value of from about 1.0 to about 1.4.

15 Claims, No Drawings

HAIR DYE HAVING IMPROVED VISCOSITY STABILITY

CROSS-REFERENCE TO RELATED APPLICATION

This application claims priority to German Patent Application No. 10 2017 216 537.5, filed Sep. 19, 2017, which is incorporated herein by reference in its entirety.

TECHNICAL FIELD

The present disclosure lies in the field of cosmetics. The subject of the present disclosure is constituted by agents for dyeing keratin fibers, which agents are produced by mixing one or more oxidation dye precursors used in their salt form and one or more water-soluble salts of barium and/or of calcium. A characterising feature here of these agents is that the molar ratio of the oxidation dye precursors in salt form to the barium and calcium salts used in the agent lies at a value of from about 1.0 to about 1.4.

BACKGROUND

A further subject of the present disclosure is a multi-component packaged unit (kit-of-parts) which comprises the above-mentioned agent in addition to an oxidizing agent preparation.

A further subject is also a method in which the above-described agents or multi-component packaged units are used.

Changing the colour of keratin fibers, in particular hair, is an important field of modern cosmetics. The appearance of the hair can thus be adapted both to current trends and to the individual desire of the individual consumer. What are known as oxidation dyes are used to produce permanent intense colorings having good fastness properties. Such dyes usually contain oxidation dye precursors, or what are known as developer components and coupler components. The developer components form the actual colorants under the influence of oxidizing agents or atmospheric oxygen with one another or with coupling to one or more coupler components. The oxidation dyes are exemplified by intense, excellent, long-lasting colour results. However, for naturally acting dyes, a mixture of a larger number of oxidation dye precursors can be used.

Oxidation dye precursors of the developer type are typically based on the basic structure of p-phenylenediamine, of p-aminophenol, or also on the structure of heterocyclic di- or polyamino compounds. Substances of this type are extremely sensitive to atmospheric oxygen. On account of this high reactivity, the use of developers in the form of their free compound—i.e. for example in the form of the free, non-stabilised p-phenylenediamine—is associated with various disadvantages: The compounds themselves have poor storage stability and quickly react prematurely in particular in solution, and in so doing form undesirable compounds. On account of the premature breakdown, the specified content of oxidation dye precursor can deviate significantly from the actual content in the stored formulation.

In order to avoid these disadvantages, oxidation dye precursors of the developer type are therefore generally not used in the form of their free compounds, but instead in stabilised form. For stabilisation, the oxidation dye precursors are converted into their physiologically acceptable salts, i.e. the amino groups present in the substances are converted—wholly or partially—into ammonium groups and are neutralised by counterions (chlorides, bromides, hydrogen sulfates or also sulfates). If a user wishes to dye their hair in a particularly dark hue, for example a dark brown or black shade, said user will thus use a corresponding dye with a particularly high colorant content. Due to the high content of oxidation dye precursors, the corresponding salt content in these agents is also very high.

Oxidative dyes are usually provided in the form of emulsions. Emulsions however, such as O/W emulsions, often react very sensitively to an increase of their salt content. The risk that an emulsion or a dye will separate and prove unstable under storage is therefore particularly high in the case of hues having a high colorant content. It is often also observed that the viscosity of an emulsion is influenced by the salt content. The coloring cream of a dark shade—in which the content of oxidation precursors in salt form is high accordingly—therefore often has a lower viscosity than an otherwise identical coloring cream of a lighter shade.

The commercial distribution of a certain hairdye brand generally comprises a certain portfolio of shades, from which the user can choose the sought colour. Within this portfolio, the same base cream is usually used for all shades, with different amounts of oxidation dye precursors being used in said base cream depending on the particular shade. The darker is the shade, the higher is the content of oxidation dye precursors and the higher is thus also the salt content in the emulsion. So as to be able to use the same base cream within the portfolio, it is of central importance that this cream has a constant and high stability both with use of low and with use of high colorant concentrations. The viscosity should also not exceed or drop below the specific range within this palette of shades.

BRIEF SUMMARY

An agent for dyeing keratin fibers is provided herein. The agent is produced by mixing (A) one or more oxidation dye precursors in salt form, and (B) one or more water-soluble salts of barium and/or of calcium. The molar ratio of all oxidation dye precursors in salt form (A) used in the agent to all water-soluble barium and calcium salts (B) used in the agent is from about 1.0 to about 1.4.

An agent for dyeing keratin fibers is also provided herein. The agent includes (A') one or more oxidation dye precursors of the developer type in the form of their freebase, and (B') barium sulfate and/or calcium sulfate. The molar ratio of all oxidation dye precursors of the developer type (A') included in the agent to the total amount of substance of the barium and calcium sulfate included in the agent is from about 1.0 to about 1.4.

A method for producing an agent for dyeing keratin fibers is provided herein. The method includes the following steps of (a) providing a cosmetic base formulation, (b) incorporating one or more oxidation dye precursors in salt form (A) into the base formulation, and (c) incorporating one or more water-soluble salts of barium and/or of calcium (B) into the base formulation. The molar ratio of all oxidation dye precursors in salt form (A) used in the base formulation to all water-soluble barium and calcium salts (B) used in the base formulation is from about 1.0 to about 1.4.

DETAILED DESCRIPTION

The following detailed description is merely exemplary in nature and is not intended to limit the disclosure or the application and uses of the subject matter as described herein. Furthermore, there is no intention to be bound by any theory presented in the preceding background or the following detailed description.

The object of the present disclosure was therefore to provide dyes (in particular coloring creams for oxidative colour changing) which have an improved stability with increased salt tolerance and optimised viscosity stability. A method and a production process should also be found, which make it possible to incorporate oxidation dye precursors in salt form in different amounts into a base cream, without at the same time influencing the desired viscosity of the resultant dye.

The coloring creams are generally made alkaline, and therefore this stabilisation shall also be ensured under alkaline conditions. The viscosity of the dye should remain stable independently of the used colorant concentration. The basic prerequisite here was additionally that the dyes should demonstrate the above-mentioned improvements without any compromises in respect of the further application-related properties. The colour intensities, washing fastness and light fastness of these agents therefore should not be worse than those of the agents known from the prior art and, optimally, should constitute an improvement.

During the course of the work leading to this present disclosure, it was possible to find a way of making the viscosity of the coloring creams stable and long-lasting over the desired specification range, independently of the used amount of oxidation dye precursors in salt form.

A first subject of the present disclosure is an agent for dyeing keratin fibers, in particular human hair, exemplified in that it is produced by mixing
(A) one or more oxidation dye precursors in salt form and
(B) one or more water-soluble salts of barium and/or of calcium,
wherein the molar ratio of all oxidation dye precursors in salt form (A) used in the agent to all water-soluble barium and calcium salts (B) used in the agent. i.e. the molar ratio (A)/(B), lies at a value of from about 1.0 to about 1.4.

In other words, a first subject of the present disclosure is an agent for dyeing keratin fibers, in particular human hair, exemplified in that, for its production,
(A) one or more oxidation dye precursors in salt form and
(B) one or more water-soluble salts of barium and/or of calcium are mixed,
wherein the molar ratio of all oxidation dye precursors in salt form (A) used in the agent to all water-soluble barium and calcium salts (B) used in the agent. i.e. the molar ratio (A)/(B), lies at a value of from about 1.0 to about 1.4.

In yet other words, a first subject of the present disclosure is an agent for dyeing keratin fibers, in particular human hair, produced from
(A) one or more oxidation dye precursors in salt form and
(B) one or more water-soluble salts of barium and/or of calcium,
wherein the molar ratio of all oxidation dye precursors in salt form (A) used in the agent to all water-soluble barium and calcium salts (B) used in the agent. i.e. the molar ratio (A)/(B), lies at a value of from about 1.0 to about 1.4.

Keratin Fibers

The agent is an agent for dyeing keratin fibers, in particular human hair. The agent is particularly preferably used for the oxidative dyeing of keratin fibers, in particular human hair.

The term "keratin fibers" is understood to mean wool, fur, feathers and in particular human hair. The agents as contemplated herein for oxidative changing of colour, however, can also be used in principle for changing the colour of other natural fibers, such as cotton, jute, sisal, flax or silk, modified natural fibers, such as regenerated cellulose, or nitro-, alkyl- or hydroxyalkyl-acetylcellulose.

Agent for Dyeing Keratin Fibers

The agent as contemplated herein is used for dyeing, in particular for oxidative dyeing, of keratin fibers.

What is essential and characterising for the dye is its preparation form, i.e. the agent as contemplated herein is produced by mixing one or more oxidation dye precursors (A), which are used in the form of one or more monovalent salts thereof, with (B) one or more water-soluble salts of barium and/or of calcium.

The agent forming the first subject of the present disclosure is, by definition, the preparation containing the oxidation dye precursors and is thus the coloring cream.

During this production, the oxidation dye precursors in salt form (A) and the water-soluble barium and calcium salts (B) are used in certain molar ratios to one another, which lie at values of from about 1.0 to about 1.4. In other words the oxidation dye precursors in salt form (A) are used in from about 1 to about 1.4 times molar excess.

Due to the use or mixing of the components (A) and (B), a reaction occurs in the dye that can be described as a neutralisation and/or salting out reaction:

$$\underset{x\ H_2SO_4}{\underset{NH_2}{\underset{|}{\text{Ar}}}\text{-CH}_3\text{-}NH_2} + Ba(OH)_2 \longrightarrow \underset{NH_2}{\underset{|}{\text{Ar}}}\text{-CH}_3\text{-}NH_2 + BaSO_4 + 2\ H_2O$$

In the reaction of (A) with (B), the salt-like oxidation dye precursor used previously in salt form (here the sulfate of p-toluene diamine) is converted into its free base. At the same time, the anionic counterion of the oxidation dye precursor in salt form (here the sulfate anion) reacts to form the corresponding poorly soluble barium or calcium salt (in this case barium sulfate). The barium sulfate precipitates and is then present in the form of a solid in the dye or in the coloring cream.

Since the barium sulfate in solid form has a lesser influence on the viscosity of the dye than the analogous water-soluble sulfate salt, a possibility has in this way been found to stabilise the viscosity independently of the amount of salts used originally in the agent.

If a dye is produced in this way, the oxidation dyes can be used in their stable salt form for the production, and the particularly sensitive free form of the oxidation dye precursor is only formed "in situ" in the agent itself. At the same time, all salts previously in solution are removed from the equilibrium due to the precipitation of the salts (such as barium sulfate), and therefore the ionic strength in the emulsion decreases.

In this way, high amounts of oxidation dyes in the form of their salts can be used in the agent, even in the case of very dark shades, without the viscosity of the agent or the cream being influenced undesirably.

Mixing of (A) and (B)

The agent forming the first subject of the present disclosure is produced by mixing (A) one or more oxidation precursors in the form of their monovalent or polyvalent salts and (B) one or more water-soluble salts of barium and/or of calcium.

Under mixing is understood to mean a bringing into contact or also blending.

The ingredients (A) and (B) can be mixed for example during production of the dye or coloring cream. Within the scope of an embodiment as contemplated herein, one or more oxidation dye precursors (A) present in the form of their salts for example firstly can be added to a base formulation, and then one or more water-soluble barium salts and/or calcium salts (B) can then be added to the base formulation.

Within the scope of a further formulation, it is also possible for the water-soluble barium salts and/or calcium salts (B) to be added first, and for the oxidation dye precursors (A) present in the form of their salts to then be introduced into the base.

The simultaneous introduction of (A) and (B) into the base formulation is also possible and included within the scope of the present disclosure.

Salt-Like Oxidation Precursors (A)

The agent as contemplated herein is produced by using at least one oxidation dye precursor present in its salt form (A). Oxidation dye precursors can be divided into compounds of the developer type and of the coupler type, wherein the developers are used in particular due to their greater sensitivity to oxygen in the form of their physiologically acceptable colour-changing salts (for example in the form of their sulfates, hydrogen sulfates, chlorides or bromides).

Salts are chemical compounds that are composed or positively charged cations and negatively charged anions. The oxidation precursor products are present in the form of organic salts, in which the cation is an organic compound.

Oxidation dye precursors of the developer type are usually derivatives of p-phenylenediamine, p-aminophenol, or heterocyclic compounds with at least one, preferably at least two amino groups. For conversion into their salts, the amino groups contained in these structures are protonated and have the corresponding equivalent of sulfate anions, hydrogen sulfate anions, chloride anions and/or bromide anions for neutralisation of this positive charge.

In the case of p-toluene diamine sulfate, this is for example the compound toluene diamine×$H_2SO_4$. Both amino groups are present in protonated form (in the form of ammonium ions) and the two cationic charges now contained in the molecule are neutralised by a sulfate anion ($SO_4^{2-}$). In the case of p-toluene diamine monohydrochloride, this is therefore the compound toluene diamine×HCl. One of the two amino groups is present in protonated form and has a chloride as counterion. In the case of p-toluene diamine dihydrochloride, this is the compound toluene diamine×2 HCl. Both amino groups are present in protonated form and have two chlorides as counterion. The salts of the further oxidation dyes of the developer type are composed similarly.

Oxidation dye precursors of the developer type (A) are in particular used in the form of their salts. Preferred compounds can be selected for example from phenylenediamine sulfate, phenylenediamine monohydrochloride, phenylenediamine dihydrochloride, p-toluene diamine sulfate, p-toluene diamine monohydrochloride, p-toluene diamine dihydrochloride, 2-(2-hydroxyethyl)-p-phenylenediamine sulfate, 2-(2-hydroxyethyl)-p-phenylenediamine monohydrochloride, 2-(2-hydroxyethyl)-p-phenylenediamine dihydrochloride, N,N-bis-(2-hydroxyethyl)-p-phenylenediamine sulfate, N,N-bis-(2-hydroxyethyl)-p-phenylenediamine monohydrochloride, N,N-bis-(2-hydroxyethyl)-p-phenylenediamine dihydrochloride, 2-methoxymethyl-p-phenylenediamine sulfate, 2-methoxymethyl-p-phenylenediamine monohydrochloride, 2-methoxymethyl-p-phenylenediamine dihydrochloride, p-aminophenol hydrogen sulfate, p-aminophenol monohydrochloride, 4-amino-3-methylphenol hydrogen sulfate, 4-amino-3-methylphenol chloride, 2,4,5,6-tetraaminopyrimidine monosulfate, 2,4,5,6-tetraaminopyrimidine disulfate, 2,4,5,6-tetraaminopyrimidine monohydrochloride, 2,4,5,6-tetraaminopyrimidine dihydrochloride, 2,4,5,6-tetraaminopyrimidine trihydrochloride, 2,4,5,6-tetraaminopyrimidine tetrahydrochloride, 4-hydroxy-2,5,6-triaminopyrimidine sulfate, 4-hydroxy-2,5,6-triaminopyrimidine monohydrochloride, 4-hydroxy-2,5,6-triaminopyrimidine diydrochloride, 4-hydroxy-2,5,6-triaminopyrimidine trihydrochloride, 4,5-diamino-1-(2-hydroxyethyl)-1H-pyrazole sulfate, 4,5-diamino-1-(2-hydroxyethyl)-1H-pyrazol monohydrochloride and/or 4,5-diamino-1-(2-hydroxyethyl)-1H-pyrazole dihydrochloride.

In this regard, it has been found that I particular the oxidation dye precursors present in the form of their polyvalent salts can have a particularly strong influence on the viscosity of a dye.

In particular if various developers in the form of their sulfate salts were used (such as toluene diamine×$H_2SO_4$, 2,4,5,6-tetraaaminopyrimidine×$H_2SO_4$, etc.), a particularly severe loss of viscosity was observed with an increase of the use concentration of said developers. In this case it was possible to prevent the undesirable reduction in viscosity particularly easily by mixing with the water-soluble barium and/or calcium salts (B).

In a further very particularly preferred embodiment an agent as contemplated herein is produced by mixing
(A) one or more oxidation dye precursors in the form of their polyvalent salts, in particular in the form of their sulfate salts.

In the sense of the present disclosure polyvalent salts are oxidation dye precursors, the ammonium groups of which are neutralised by a repeatedly negatively charged anion, in particular a sulfate anion ($SO_4^{2-}$) (for example toluene diamine×$H_2SO_4$).

In a further very particularly preferred embodiment an agent as contemplated herein is produced by mixing
(A) one or more oxidation dye precursors from the group of phenylenediamine sulfate, p-toluene diamine sulfate, 2-(2-hydroxyethyl)-p-phenylenediamine sulfate, N,N-bis-(2-hydroxyethyl)-p-phenylenediamine sulfate, 2-methoxymethyl-p-phenylenediamine sulfate, 2,4,5,6-tetraaminopyrimidine monosulfate, 2,4,5,6-tetraaminopyrimidine disulfate, 4-hydroxy-2,5,6-triaminopyrimidine sulfate and/or 4,5-diamino-1-(2-hydroxyethyl)-1H-pyrazole sulfate.

Oxidation dye precursors of the developer type can be contained in the agent as contemplated herein as the sole colour-changing compounds. However, it is preferred as contemplated herein if the dye additionally contains at least one oxidation dye precursor of the coupler type (referred to as coupler for short).

Within the scope of oxidative dyeing, coupler components do not result in significant dyeing, and instead always require the presence of developer components. Coupler components as contemplated herein allow at least one substitution of a chemical groups of the coupler by the oxidised form of the developer component. here, covalent bonds form between the coupler and developer component.

The coupler components generally have a greater stability to oxygen. Although in principle the couplers can also be used in the form of their salts, this is not generally necessary on account of the higher stability of this compound class. The couplers are therefore generally used in the agent in the form of their free compound (i.e. not in salt form).

At least one compound from one of the following classes is preferably selected as coupler component suitable as contemplated herein:
- m-aminophenol and/or derivatives thereof,
- m-diaminobenzene and/or derivatives thereof,
- o-diaminobenzene and/or derivatives thereof,
- o-aminophenol derivates, such as o-aminophenol,
- naphthalene derivatives with at least one hydroxy group,
- di- or trihydroxybenzene and/or derivatives thereof,
- pyridine derivatives,
- pyrimidine derivatives,
- monohydroxyindol derivatives and/or monoaminoindol derivatives,
- monohydroxyindoline derivatives and/or monoaminoindoline derivatives,
- pyrazolone derivative, such as 1-phenyl-3-methylpyrazol-5-one,
- morpholine derivatives, such as 6-hydroxybenzomorpholine or 6-aminobenzomorpholine,
- quinoxaline derivatives, such as 6-methyl-1,2,3,4-tetrahydroquinoxaline.

In a further embodiment an agent as contemplated herein contains at least one oxidation dye precursor of the coupler type, which is selected from the group of 3-aminophenol, 5-amino-2-methylphenol, 3-amino-2-chloro-6-methylphenol, 2-hydroxy-4-aminophenoxyethanol, 5-amino-4-chloro-2-methylphenol, 5-(2-hydroxyethyl)-amino-2-methylphenol, 2,4-dichloro-3-aminophenol, 2-aminophenol, 3-phenylenediamine, 2-(2,4-diaminophenoxy)ethanol, 1,3-bis(2,4-diaminophenoxy)propane, 1-methoxy-2-amino-4-(2-hydroxyethylamino)benzene, 1,3-bis(2,4-diaminophenyl)propane, 2,6-bis(2'-hydroxyethylamino)-1-methylbenzene, 2-({3-[(2-hydroxyethyl)amino]-4-methoxy-5-methylphenyl}amino)ethanol, 2-({3-[(2-hydroxyethyl)amino]-2-methoxy-5-methylphenyl}amino)ethanol, 2-({3-[(2-hydroxyethyl)amino]-4,5-dimethylphenyl}amino)ethanol, 2-[3-morpholin-4-ylphenyl)amino]ethanol, 3-amino-4-(2-methoxyethoxy)-5-methylphenylamine, 1-amino-3-bis-(2-hydroxyethyl)aminobenzene, resorcinol, 2-methylresorcinol, 4-chlororesorcinol, 1,2,4-trihydroxybenzene, 2-amino-3-hydroxypyridine, 3-amino-2-methylamino-6-methoxypyridine, 2,6-dihydroxy-3,4-dimethylpyridine, 3,5-diamino-2,6-dimethoxypyridine, 1-phenyl-3-methylpyrazol-5-one, 1-naphthol, 1,5-dihydroxynaphthalene, 2,7-dihydroxynaphthalene, 1,7-dihydroxynaphthalene, 1,8-dihydroxynaphthalene, 4-hydroxyindole, 6-hydroxyindole, 7-hydroxyindole, 4-hydroxyindoline, 6-hydroxyindoline and 7-hydroxyindoline.

Depending on the desired colour result, oxidation precursors of the developer and coupler type are used in different amounts in the dye.

If dyeing in a blonde shade is desired, the use of oxidation precursors in a total amount below about 0.3% by weight is usually sufficient.

If, however, the user wishes to achieve dyeing in a very dark shade, for example in a dark brown shade or in a black shade, this necessitates the use of oxidation precursors in a total amount of at least about 2.0% by weight, often about 3.0% by weight, and in the case of particularly dark shades (black) even above about 4.5% by weight (in relation to the total weight of the agent as contemplated herein, i.e. the coloring cream made alkaline).

The higher is the colorant content, the more difficult it is to stabilise the agent. In this regard it has been found that in particular the stabilisation of brown or black shades is possible by the previously described mixing of components (A) and (B).

In a further very particularly preferred embodiment an agent as contemplated herein is exemplified in that the total amount of all oxidation dye precursors in salt form (A) used in the agent, in relation to the total weight of the agent, is from about 0.1 to about 6.5% by weight, preferably from about 0.5 to about 4.0% by weight, more preferably from about 0.8 to about 4.0% by weight, even more preferably from about 1.1 to about 4.0% by weight, and very particularly preferably from about 2.0 to about 4.0% by weight.

Water-Soluble Barium Salts and Calcium Salts (B)

A characterising feature of the agent as contemplated herein is its production, which is achieved by mixing the oxidation dye precursors used in salt form (A) with the one or more water-soluble salts of barium and/or of calcium (B).

The term "water-soluble salts of barium and of calcium" is understood to mean salts that have a water solubility at about 20° C. of at least about 1 g/l (1 g per litre of water).

Preferred water-soluble salts of barium and of calcium are, for example
- barium hydroxide $Ba(OH)_2$, solubility about 72 g per litre of water
- barium chloride $BaCl_2$, solubility about 375 g per litre of water
- barium nitrate $Ba(NO_3)_2$, solubility about 90 g per litre of water
- barium bromide $BaBr_2$, solubility about 1041 g per litre of water
- barium acetate $Ba(OOCCH_3)_2$, solubility about 720 g per litre of water
- calcium hydroxide $Ca(OH)_2$, solubility about 1.7 g per litre of water
- calcium chloride $CaCl_2$, solubility about 740 g per litre of water
- calcium nitrate $Ca(NO_3)_2$, solubility about 1470 g per litre of water
- calcium bromide $CaBr_2$, solubility about 1420 g per litre of water
- calcium acetate $Ca(OOCCH_3)_2$, solubility about 400 g per litre of water The hydrates of the aforementioned salts are also included as contemplated herein.

Ver particularly preferred water-soluble salts of barium are those selected from
- barium hydroxide $Ba(OH)_2$, solubility about 72 g per litre of water
- barium chloride $BaCl_2$, solubility about 375 g per litre of water
- barium nitrate $Ba(NO_3)_2$, solubility about 90 g per litre of water
- barium bromide $BaBr_2$, solubility about 1041 g per litre of water
- barium acetate $Ba(OOCCH_3)_2$, solubility about 720 g per litre of water The hydrates of the aforementioned salts are also preferred.

In a further very particularly preferred embodiment an agent as contemplated herein is produced by mixing
(B) one or more water-soluble salts from the group of barium hydroxide, barium chloride, barium nitrate, barium bromide, barium acetate, calcium hydroxide, calcium chloride, calcium nitrate, calcium bromide and/or calcium acetate, very particularly preferably from the group of barium hydroxide, barium chloride, barium nitrate, barium bromide and/or barium acetate.

Within the scope of a further embodiment it is also very particularly preferred to use one or more compounds from the group of barium hydroxide ($Ba(OH)_2$) and calcium hydroxide ($Ca(OH)_2$) as water-soluble barium and calcium salts (B).

In a further very particularly preferred embodiment, an agent as contemplated herein is produced by mixing (B) one or more water-soluble salts from the group of barium hydroxide and calcium hydroxide.

Calcium hydroxide and barium hydroxide on the one hand are capable of precipitating the anions introduced by the oxidation dye precursor, but in addition can also be used for neutralisation or alkalisation of the dye. The salt load created with this neutralisation reaction is very particularly low.

Molar Ratio (A)/(B)

A further feature essential to the present disclosure is the molar ratio (A)/(B) of the ingredients (A) and (B) contained in the agent. This molar ratio as contemplated herein lies at a value of from about 1.0 to about 1.4.

A molar ratio (A)/(B) is understood to be the molar ratio of all oxidation dye precursors (A) used in salt form in the agent to all water-soluble barium and calcium salts (B) used in the agent.

If the molar ratio (A)/(B) is about 1.0, the oxidation dye precursors (A) in salt form and the water-soluble barium and calcium salts (B) are used in equimolar amounts. With a molar ratio (A)/(B) of about 1.0, it is ensured that the total amount of substance of the anions from the oxidation dye precursors in salt form (A) can be fully converted into the corresponding insoluble salts by reaction with the barium and calcium salts (B).

For toxicological reasons, however, it should be ensured that no excess of soluble calcium salts or in particular soluble barium salts remains in the dye. For this reason, it is preferred to use the oxidation dye precursors in salt form (A) in an amount up to about 1.4 times molar excess.

If the molar ratio (A)/(B) is about 1.4, a 1.4 times molar excess of oxidation dye precursors in salt form (A) is present in the agent.

In this way, it is ensured that a significant proportion of the anions from the oxidation dye precursors in salt form (A) is still converted into the insoluble barium and calcium salts. At the same time, the excess of (A), however, is so high that no residues of water-soluble barium and calcium salts (B) remain in the agent.

The presence of the insoluble salts (such as barium sulfate or calcium sulfate) is not associated with any disadvantages either in respect of the intended application or from a toxicological viewpoint.

It has proven to be very particularly preferred if the molar ratio of all oxidation dye precursors in salt form (A) used in the agent to all water-soluble barium and calcium salts (B) used in the agent, i.e. the molar ratio (A)/(B) lies at a value of from about 1.0 to about 1.35, preferably at from about 1.0 to about 1.30, more preferably at from about 1.0 to about 1.25, and very particularly preferably at from about 1.05 to about 1.25.

In a further very particularly preferred embodiment an agent as contemplated herein is exemplified in that the molar ratio of all oxidation dye precursors in salt form (A) used in the agent to all water-soluble barium and calcium salts (B) used in the agent, i.e. the molar ratio (A)/(B) lies at a value of from about 1.0 to about 1.35, preferably at from about 1.0 to about 1.30, more preferably at from about 1.0 to about 1.25, and very particularly preferably at from about 1.05 to about 1.25.

Example

The following were introduced, with stirring, into a base formulation (100 g)

1.0 g (4.16 mmol) 4,5-diamino-1-(2-hydroxyethyl)-1H-pyrazole sulfate, molar mass=240.23 g/mol

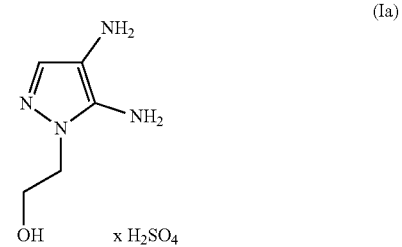

(Ia)

1.0 g (4.54 mmol) p-toluene diamine sulfate, molar mass=220.25 g/mol und

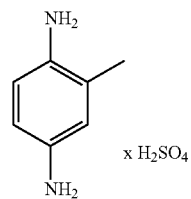

0.5 g (1.99 mol) 2-(2-hydroxyethyl)-p-phenylenediamine sulfate, molar mass=250.27 g/mol

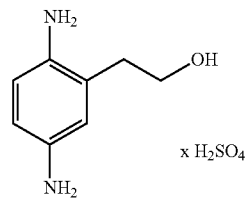 [SMILES: Nc1ccc(N)c(CCO)c1]

Resorcinol and 2-methylresorcinol (not salts) were added as couplers to the base cream. The total amount of substance of the oxidation dye precursors in salt form (A) contained in the agent was 4.16 mmol+4.54 mmol+1.99 mmol=10.69 mmol (millimol). 1.71 g (10 mmol) barium hydroxide $Ba(OH)_2$ (molar mass=171.34 g/mol) were then incorporated into the agent, with stirring.

The molar ratio (A)/(B) was 10.69 mmol/10 mmol=1.069.

Dyes in the Form of an Emulsion

The previously described influences of the salt concentration on the viscosity of the agent can be observed in particular if the dye is provided to the user in the form of an emulsion.

In an emulsion a finely distributed mixture of two liquids, for example fat bodies (oils, fatty alcohols, hydrocarbons or also fatty acid triglycerides) and water, is provided. A theory in respect of emulsions is that one of the liquids (phase) forms small droplets present distributed in the other liquid (phase). The phase which forms the droplets is referred to as the inner phase or also disperse phase. The phase in which the droplets float is referred to as the outer phase or also the continuous phase.

In the case of emulsions that comprise a water phase and an oil phase, a distinction is made between oil-in-water emulsions (O/W emulsions) and water-in-oil emulsions (W/O emulsions). Conventional O/W emulsions are often described in the literature as oil droplets, which are dispersed in the continuous water phase and are stabilised at the interface of both phases by surfactants or emulsifiers. The latter form a film around the oil droplets and are thus capable of reducing the surface tension. In complex cosmetic formulations, however, multiple different ingredients are generally used, whereby complex multi-phase systems are produced.

Many agents for dyeing keratin fibers or human hair are present in the form of emulsions. An emulsion of this kind can then be referred to as stable if the fusion of the droplets can be prevented by a sufficiently high energy barrier. Generally, this energy barrier is formed by the film formed by the one or more emulsifiers at the surface of the particular droplet. If the emulsion is unstable, it breaks and separates into oil and water phase. Cosmetic products, in particular hair dyes, often have to endure storage periods of many months. It is an essential quality requirement that the dyes in the form of an emulsion remain stable over the entire storage period and do not separate during storage.

The formulation in the form of an emulsion (for example an oil-in-water emulsion) can be attained by incorporating fatty constituents and/or emulsifiers into an aqueous carrier. Fatty bodies and/or emulsifier together form an emulsion which is preferably an oil-in-water emulsion. Water is in this case the outer phase or also the continuous phase.

The agent as contemplated herein particularly preferably contains—in relation to its total weight—from about 50 to about 95% by weight, preferably from about 55 to about 90% by weight, more preferably from about 60 to about 85% by weight, and very particularly preferably from about 65 to about 80% by weight of water.

In a further very particularly preferred embodiment an agent as contemplated herein is present in the form of an oil-in-water emulsion (O/W emulsion).

In other words, what is very particularly preferred is an agent in the form of an O/W emulsion for dyeing keratin fibers, in particular human hair, exemplified in that it is produced by mixing
(A) one or more oxidation dye precursors in salt form and
(B) one or more water-soluble salts of barium and/or of calcium,
wherein the molar ratio of all oxidation dye precursors in salt form (A) used in the agent to all water-soluble barium and calcium salts (B) used in the agent. i.e. the molar ratio (A)/(B), lies at a value of from about 1.0 to about 1.4.

In yet other words, what is very particularly preferred is an agent in the form of an O/W emulsion for dyeing keratin fibers, in particular human hair, exemplified in that, in its production,
(A) one or more oxidation dye precursors in salt form and
(B) one or more water-soluble salts of barium and/or of calcium, are mixed, wherein the molar ratio of all oxidation dye precursors in salt form (A) used in the agent to all water-soluble barium and calcium salts (B) used in the agent. i.e. the molar ratio (A)/(B), lies at a value of from about 1.0 to about 1.4.

The use of $C_{12}$-$C_{30}$ fatty alcohols has proven to be particularly well suited for the production of dyes in the form of an emulsion.

The $C_{12}$-$C_{30}$ fatty alcohols can be saturated, mono- or polyunsaturated, linear or branched fatty alcohols with from about 12 to about 30 C atoms.

Examples of preferred linear saturated $C_{12}$-$C_{30}$ fatty alcohols are dodecan-1-ol (dodecyl alcohol, lauryl alcohol), tetradecan-1-ol (tetradecyl alcohol, myristyl alcohol), hexadecan-1-ol (hexadecyl alcohol, cetyl alcohol, palmityl alcohol), octadecan-1-ol (octadecyl alcohol, stearyl alcohol), arachyl alcohol (eicosan-1-ol), heneicosyl alcohol (heneicosan-1-ol) and/or behenyl alcohol (docosan-1-ol).

Preferred linear unsaturated fatty alcohols are (9Z)-octadec-9-en-1-ol (oleyl alcohol), (9E)-octadec-9-en-1-ol (elaidyl alcoh+1), (9Z,12Z)-octadeca-9,12-dien-1-ol (linoleyl alcohol), (9Z,12Z,15Z)-octadeca-9,12,15-trien-1-ol (linolenoyl alcohol), gadoleyl alcohol ((9Z)-eicos-9-en-1-ol), arachidonic alcohol ((5Z,8Z,11Z,14Z)-eicosa-5,8,11,14-tetraen-1-ol), erucyl alcohol ((13Z)-docos-13-en-1-ol) and/or brassidyl alcohol ((13E)-docosen-1-ol).

The preferred representatives of branched fatty alcohols are 2-octyl-dodecanol, 2-hexyl-dodecanol and/or 2-butyl-dodecanol.

In a further very particularly preferred embodiment an agent as contemplated herein contains one or more C12-C30 fatty alcohols.

Agents with very particularly preferred storage stability could be obtained if the agents—in relation to their total weight—contained one or more $C_{12}$-$C_{30}$ fatty alcohols in a total amount of from about 0.1 to about 20.0% by weight, preferably from about 5.0 to about 15.0% by weight, more preferably from about 10.0 to about 13.0% by weight, and very particularly preferably from about 10.5 to about 12.5% by weight. Here, all values in % by weight relate again to the total amount of the $C_{16}$-$C_{18}$ fatty alcohols (d), which is placed in relation to the total weight of the agent.

In order to form the emulsion, the agents as contemplated herein usually also contain one or more emulsifiers. Emulsifiers are surface-active substances that are also referred to as surfactants: They are preferably selected from anionic, zwitterionic, amphoteric and non-ionic surfactants and emulsifiers.

Agents suitable as contemplated herein are exemplified in that the agent additionally contains at least one anionic surfactant. Preferred anionic surfactants are fatty acids, alkyl sulfates, alkyl ether sulfates and ether carboxylic acids with from about 10 to about 20 C atoms in the alkyl group and up to about 16 glycol ether groups in the molecule.

Agents that are suitable as contemplated herein are exemplified in that the agent additionally contains at least one zwitterionic surfactant. Preferred zwitterionic surfactants are betaines, N-alkyl-N,N-dimethylammoniumglycinates, N-acyl-aminopropyl-N,N-dimethylammoniumglycinates, and 2-alkyl-3-carboxymethyl-3-hydroxyethyl-imidazolines. A preferred zwitterionic surfactant is known under the INCI name Cocamidopropyl Betaine.

Agents that are suitable as contemplated herein are exemplified in that the agent additionally contains at least one amphoteric surfactant. Preferred amphoteric surfactants are N-alkyl glycine, N-alkyl propionic acids, N-alkyl amino butyric acids, N-alkyl imino dipropionic acids, N-hydroxyethyl-N-alkyl amidopropyl glycine, N-alkyl taurine, N-alkyl sarcosine, 2-alkyl amino propionic acids and alkyl amino acetic acids. Particularly preferred amphoteric surfactants are N-coco alkyl amino propionate, coco acylamino ethylamino propionate and $C_{12}$-$C_{18}$ acyl sarcosine.

It has also proven advantageous if the agents contain further, non-ionic surfactant substances. Preferred non-ionic surfactants are alkylpolyglycosides and alkylene oxide addition products with fatty alcohols and fatty acids, with in each case from about 2 to about 30 mol ethylene oxide per mol fatty alcohol or fatty acid. Preparations having excellent properties are also obtained if they contain fatty acid esters of ethoxylated glycerol as non-ionic surfactants.

Suitable non-ionic surfactants can be, for example, Ceteareth-2, Steareth-2, Ceteth-2, Oleth-2, Ceteareth-3, Steareth-3, Ceteth-3, Oleth-3, Ceteareth-4, Steareth-4, Ceteth-4, Oleth-4, Ceteareth-5, Steareth-5, Ceteth-5 and/or Oleth-5, Ceteareth-30, Steareth-30, Ceteth-30, Oleth-30, Ceteareth-50, Steareth-50, Ceteth-50, Oleth-50, Ceteareth-100, Steareth-100, Ceteth-100 and Oleth-100.

The non-ionic, zwitterionic or amphoteric surfactants are used in amounts of from about 0.1 to about 45% by weight, preferably from about 1 to about 30% by weight, and very particularly preferably from about 1 to about 15% by weight, in relation to the total amount of the ready-to-use agent.

What is very particularly preferred is therefore an agent for dyeing keratin fibers, in particular human hair, exemplified in that it is produced by mixing
(A) one or more oxidation dye precursors in salt form and
(B) one or more water-soluble salts of barium and/or calcium, wherein
the molar ratio of all oxidation dye precursors in salt form (A) used in the agent to all water-soluble barium and calcium salts (B) used in the agent, i.e. the molar ratio (A)/(B), lies at a value of from about 1.0 to about 1.4, and
the agent contains one or more $C_{12}$-$C_{30}$ fatty alcohols, and
the agent contains one or more surfactants from the group of anionic, non-ionic, zwitterionic, amphoteric and cationic surfactants.

What is very particularly preferred is therefore also an agent for dyeing keratin fibers, in particular human hair, exemplified in that it is produced by mixing
(A) one or more oxidation dye precursors in salt form and
(B) one or more water-soluble salts of barium and/or calcium, wherein
the molar ratio of all oxidation dye precursors in salt form (A) used in the agent to all water-soluble barium and calcium salts (B) used in the agent, i.e. the molar ratio (A)/(B), lies at a value of from about 1.0 to about 1.4, and
the agent contains one or more $C_{12}$-$C_{30}$ fatty alcohols, and
the agent contains one or more surfactants from the group of anionic surfactants.

What is very particularly preferred is therefore also an agent for dyeing keratin fibers, in particular human hair, exemplified in that it is produced by mixing
(A) one or more oxidation dye precursors in salt form and
(B) one or more water-soluble salts of barium and/or calcium, wherein
the molar ratio of all oxidation dye precursors in salt form (A) used in the agent to all water-soluble barium and calcium salts (B) used in the agent, i.e. the molar ratio (A)/(B), lies at a value of from about 1.0 to about 1.4, and
the agent contains one or more $C_{12}$-$C_{30}$ fatty alcohols, and
the agent contains one or more surfactants from the group of non-ionic surfactants.

What is very particularly preferred is therefore also an agent for dyeing keratin fibers, in particular human hair, exemplified in that it is produced by mixing
(A) one or more oxidation dye precursors in salt form and
(B) one or more water-soluble salts of barium and/or calcium,
wherein
the molar ratio of all oxidation dye precursors in salt form (A) used in the agent to all water-soluble barium and calcium salts (B) used in the agent, i.e. the molar ratio (A)/(B), lies at a value of from about 1.0 to about 1.4, and
the agent contains one or more $C_{12}$-$C_{30}$ fatty alcohols, and
the agent contains one or more surfactants from the group of zwitterionic or amphoteric surfactants.

What is very particularly preferred is therefore also an agent for dyeing keratin fibers, in particular human hair, exemplified in that, for its production,
(A) one or more oxidation dye precursors in salt form and
(B) one or more water-soluble salts of barium and/or calcium are mixed,
wherein
the molar ratio of all oxidation dye precursors in salt form (A) used in the agent to all water-soluble barium and calcium salts (B) used in the agent, i.e. the molar ratio (A)/(B), lies at a value of from about 1.0 to about 1.4, and
the agent contains one or more $C_{12}$-$C_{30}$ fatty alcohols, and
the agent contains one or more surfactants from the group of anionic, non-ionic, zwitterionic, amphoteric and cationic surfactants.

What is very particularly preferred is therefore also an agent for dyeing keratin fibers, in particular human hair, exemplified in that, for its production,
(A) one or more oxidation dye precursors in salt form and
(B) one or more water-soluble salts of barium and/or calcium are mixed,
wherein
the molar ratio of all oxidation dye precursors in salt form (A) used in the agent to all water-soluble barium and calcium salts (B) used in the agent, i.e. the molar ratio (A)/(B), lies at a value of from about 1.0 to about 1.4, and
the agent contains one or more $C_{12}$-$C_{30}$ fatty alcohols, and
the agent contains one or more surfactants from the group of anionic surfactants.

What is very particularly preferred is therefore also an agent for dyeing keratin fibers, in particular human hair, exemplified in that, for its production,
(A) one or more oxidation dye precursors in salt form and
(B) one or more water-soluble salts of barium and/or calcium are mixed,
wherein
the molar ratio of all oxidation dye precursors in salt form (A) used in the agent to all water-soluble barium and calcium salts (B) used in the agent, i.e. the molar ratio (A)/(B), lies at a value of from about 1.0 to about 1.4, and
the agent contains one or more $C_{12}$-$C_{30}$ fatty alcohols, and
the agent contains one or more surfactants from the group of non-ionic surfactants.

What is very particularly preferred is therefore also an agent for dyeing keratin fibers, in particular human hair, exemplified in that, for its production,
(A) one or more oxidation dye precursors in salt form and
(B) one or more water-soluble salts of barium and/or calcium are mixed, wherein
 the molar ratio of all oxidation dye precursors in salt form (A) used in the agent to all water-soluble barium and calcium salts (B) used in the agent, i.e. the molar ratio (A)/(B), lies at a value of from about 1.0 to about 1.4, and
 the agent contains one or more $C_{12}$-$C_{30}$ fatty alcohols, and the agent contains one or more surfactants from the group of zwitterionic or amphoteric surfactants.

Substantive Dyes

In addition to the oxidation dye precursors or instead of these, the agents as contemplated herein can contain at least one substantive dye. These are colorants that are taken up directly on the hair and do not require an oxidative process in order to form the colour. Substantive dyes are usually nitrophenylenediamines, nitroaminophenols, azo dyes, anthraquinones, triarylmethane dyes or indophenols.

Substantive dyes can be divided into anionic, cationic and non-ionic substantive dyes.

In particular, non-ionic nitro and quinone dyes and neutral azo dyes are suitable as non-ionic substantive dyes. Preferred non-ionic substantive dyes are the compounds known under the following international names or trade names: HC Yellow 2, HC Yellow 4, HC Yellow 5, HC Yellow 6, HC Yellow 12, HC Orange 1, Disperse Orange 3, HC Red 1, HC Red 3, HC Red 10, HC Red 11, HC Red 13, HC Red BN, HC Blue 2, HC Blue 11, HC Blue 12, Disperse Blue 3, HC Violet 1, Disperse Violet 1, Disperse Violet 4, Disperse Black 9, and 1,4-aiamino-2-nitrobenzene, 2-amino-4-nitrophenol, 1,4-bis-(2-hydroxyethyl)-amino-2-nitrobenzene, 3-nitro-4-(2-hydroxyethyl)-aminophenol, 2-(2-hydroxyethyl)amino-4,6-dinitrophenol, 4-[(2-hydroxyethyl)amino]-3-nitro-1-methylbenzene, 1-amino-4-(2-hydroxyethyl)-amino-5-chloro-2-nitrobenzene, 4-amino-3-nitrophenol, 1-(2'-ureidoethyl)amino-4-nitrobenzene, 2-[(4-amino-2-nitrophenyl)amino]-benzoic acid, 6-nitro-1,2,3,4-tetrahydroquinoxaline, 2-hydroxy-1,4-naphthoquinone, picramic acid and colour-changing salts thereof, 2-amino-6-chloro-4-nitrophenol, 4-ethylamino-3-nitrobenzoic acid and 2-chloro-6-ethylamino-4-nitrophenol.

Anionic substantive dyes carry at least one negative charge and are also referred to in the literature as acid dyes. Preferred anionic substantive dyes are the compounds known under the international names or trade names: bromophenol blue, tetrabromophenol blue, Acid Yellow 1, Yellow 10, Acid Yellow 23, Acid Yellow 36, Acid Orange 7, Acid Red 33, Acid Red 52, Pigment Red 57:1, Acid Blue 7, Acid Green 50, Acid Violet 43, Acid Black 1 and Acid Black 52.

Cationic dyes are exemplified by the presence of at least one positive charge. In the English literate, cationic dyes are also referred to as "basic dyes". Preferred cationic substantive dyes are Basic Blue 7, Basic Blue 26, Basic Violet 2 and Basic Violet 14, Basic Yellow 57, Basic Red 76, Basic Blue 16, Basic Blue 347 (Cationic Blue 347/Dystar), HC Blue No. 16, Basic Blue 99, Basic Brown 16, Basic Brown 17, Yellow 87, Basic Orange 31 and Basic Red 51.

Resultant Dyes

As already described beforehand, the agents as contemplated herein are produced by mixing one or more oxidation dye precursors used in salt form (A) with one or more water-soluble barium salts or calcium salts (B).

In particular, oxidation dye precursors of the developer type (A') are highly reactive and very sensitive to oxidative conditions. For comfortable production, in order to observe the specified amounts, and in order to obtain an aesthetically pleasing agent, practically all oxidation dye precursors of the developer type are therefore used in their salt form.

By mixing (A) (or (A')) and (B), these salts—in situ—are converted into their free compounds. Furthermore, the counterions of the oxidation dye precursors in salt form—for example the sulfates—precipitates as barium sulfate or calcium sulfate and in the form of their solid have only a small influence on the viscosity and storage stability of the agent.

The result of this reaction is that the finished, prepared agent, i.e. the agent used ultimately by the user for the dyeing process, contains other ingredients. The agent provided to the user contains (A') one or more oxidation dye precursors of the developer type in the form of their free base and (B') barium sulfate and/or calcium sulfate.

A second subject of the present disclosure is therefore an agent for dyeing keratin fibers, in particular human hair, containing
 (A') one or more oxidation dye precursors of the developer type in the form of their free base, and
 (B') barium sulfate and/or calcium sulfate
 wherein the molar ratio of all oxidation dye precursors of the developer type (A') contained in the agent to the total amount of substance of the barium and calcium sulfate contained in the agent, i.e. the molar ratio (A')/(B'), lies at a value of from about 1.0 to about 1.4.

Oxidation dye precursors of the developer type in the form of their free base are understood to mean compounds that are not present in salt form, but instead the (basic) amino groups thereof in free form, i.e. in the form of the amino group itself.

Since the ingredients (A) and (B) are used in certain molar ratios to one another, the resultant ingredients (A') and (B') are also contained in the agent in the same molar ratios.

In a particularly preferred embodiment an agent as contemplated herein is therefore exemplified in that the molar ratio of all oxidation dye precursors of the developer type (A') used in the agent to the total amount of substance of the barium sulfate and calcium sulfate (B') contained in the agent, i.e. the molar ratio (A')/(B), lies at a value of from about 1.0 to about 1.35, preferably at from about 1.0 to about 1.30, more preferably at from about 1.0 to about 1.25 and very particularly preferably at from about 1.05 to about 1.25.

The one or more oxidation dye precursors of the developer type in the form of their free base (A') is/are formed from the oxidation dye precursors of the developer type in salt form. The following can be cited here: phenylenediamine, p-toluene diamine, 2-(2-hydroxyethyl)-p-phenylenediamine, N,N-bis-(2-hydroxyethyl)-p-phenylenediamine, 2-methoxymethyl-p-phenylenediamine, 2,4,5,6-tetraaminopyrimidine, 4-hydroxy-2,5,6-triaminopyrimidine and/or 4,5-diamino-1-(2-hydroxyethyl)-1H-pyrazole (in each case as free compound, not as salt).

In a further particularly preferred embodiment an agent as contemplated herein contains
(A') one or more oxidation dye precursors of the developer type in the form of their free base, selected from the group of phenylenediamine, p-toluene diamine, 2-(2-hydroxyethyl)-p-phenylenediamine, N,N-bis-(2-hydroxyethyl)-p-phenylenediamine, 2-methoxymethyl-p-phenylenediamine, 2,4,5,6-tetraaminopyrimidine, 4-hydroxy-2,5,6-triaminopyrimidine and 4,5-diamino-1-(2-hydroxyethyl)-1H-pyrazole.

Alkalising Agent

The agents as contemplated herein are used as coloring creams in the oxidative dyeing of keratin fibers, in particular hair. The oxidative dyeing of hair is generally performed at a neutral, in particular alkaline pH value. For this reason, the agents as contemplated herein are made alkaline and contain at least one alkalising agent.

The coloring creams as contemplated herein. preferably have a pH value in the range of from about 7 to about 12, preferably a pH value in the range of from about 8.0 to about 11.5. The pH values in the sense of the present disclosure are pH values that were measured at a temperature of about 22° C.

The alkalising agents that can be used to adjust the pH value are typically selected from inorganic salts, in particular of the alkali and alkaline earth metals, organic alkalising agents, in particular amines, basic amino acids and alkanolamines, and ammonia. Organic alkalising agents that can be used as contemplated herein are preferably selected from alkanolamines from primary, secondary or tertiary amines with a $C_2$-$C_6$ alkyl basic structure, carrying at least one hydroxyl group. Particularly preferred alkanolamines are selected from 2-aminoethan-1-ol (monoethanolamine), 2-amino-2-methylpropan-1-ol, 2-amino-2-methyl-propan-1, 3-diol and triethanolamine. Inorganic alkalising agents that can be used as contemplated herein are preferably selected from the group formed from sodium hydroxide, potassium hydroxide, calcium hydroxide, barium hydroxide, sodium phosphate, potassium phosphate, sodium silicate, potassium silicate, sodium carbonate, and potassium carbonate, preferably sodium hydroxide and/or potassium hydroxide. The basic amino acids are preferably selected from the group formed from L-arginine, D-arginine, D/L-arginine, L-lysine, D-lysine, D/L-lysine, particularly preferably L-arginine, D-arginine ad D/L-arginine. Lastly, a further preferred alkalising agent is ammonia.

In a further very particularly preferred embodiment, an agent as contemplated herein contains one or more alkalising agent(s) from the group of ammonia, 2-aminoethan-1-ol, 2-amino-2-methylpropane-1-ol, 2-amino-2-methyl-propan-1,3-diol, L-arginine, D-arginine, D/L-arginine, L-lysine, D-lysine and D/L-lysine.

In principle, the substantive dyes can be contained in the agent as contemplated herein in a total amount of from about 0.001 to about 10%.

Viscosity

As described beforehand, coloring creams for the production of which the constituents (A) and (B) have been mixed (or coloring creams containing the constituents (A') and (B')) can be produced in the form of a particularly stable emulsion also having excellent viscosity stability. In this context, viscosity stability is understood to mean that the emulsion reacts to changes of the used salt content merely with minimal viscosity fluctuations.

The viscosities were measured when performing the work leading to this present disclosure using a Haake Rheostress 6000 viscometer at about 20° C. (20° C./Haake Rheostress 6000/measured with cone 35/1 geometry, diameter 35 mm and 1° angle/shear rate 7.2 $s^{-1}$).

By using the constituents (A) and (B), it could be ensured that the viscosities of the dyes (or the coloring creams) as contemplated herein were in the range of from about 10,000 to about 30,000 mPas, preferably from about 10,000 to about 28,000 mPas, and very particularly preferably from about 10,000 to about 25,000 mPas (20° C./Haake Rheostress 6000/measured with cone 35/1 geometry, diameter 35 mm and 1° angle/shear rate 7.2 $s^{-1}$).

In a further very particularly preferred embodiment an agent as contemplated herein has a viscosity of from about 10,000 to about 30,000 mPas, preferably from about 10,000 to about 28,000 mPas, and very particularly preferably from about 10,000 to about 25,000 mPas (20° C./Haake Rheostress 6000/measured with cone 35/1 geometry, diameter 35 mm and 1° angle/shear rate 7.2 $s^{-1}$).

Multi-Component Packaging Unit (Kit-of-Parts)

The agents as contemplated herein are agents for oxidatively changing the colour of keratin fibers. In particular, they are agents for the dyeing, especially oxidative dyeing, of human hair. For initiation of the oxidative dyeing process and in order to form the oxidation dyes, the coloring cream is mixed just before use with an oxidizing agent preparation. In this way, the ready-to-use oxidative dye is produced, which is applied to the user's hair.

In order to avoid incompatibilities and in order to prevent a premature, undesirable colorant formation, the coloring cream and the oxidizing agent preparation necessary for the oxidative coloring are always packaged separately from one another and are brought into contact with one another just before use. For the consumer, the two components are provided preferably in the form of a multi-component packaged unit (kit-of-parts).

A third subject of the present disclosure is therefore a multi-component packaged unit (kit-of-parts) for the oxidative dyeing of keratin fibers, in particular human hair, comprising, packaged separately from one another
  a first container containing a cosmetic agent (I) and
  a second container containing a cosmetic agent (II), wherein
  the agent (I) in the first container is a dye, as has been disclosed in detail in the description of the first and second subjects of the present disclosure, and
  the agent (II) in the second container is an oxidizing agent preparation containing hydrogen peroxide.

Oxidizing Agent Preparation (B)

The oxidizing agent preparation (B) contains hydrogen peroxide as oxidizing agent. The hydrogen peroxide can be provided either as hydrogen peroxide itself or also in the form of its solid addition products with organic or inorganic compounds, such as urea, melamine and sodium borate.

The amount of oxidizing agent in the oxidizing agent preparation (B)—in relation to the total weight of the oxidizing agent preparation (B)—is preferably from about 0.5 to about 12% by weight, preferably from about 2 to about 10% by weight, particularly preferably from about 3 to about 6% by weight (calculated as 100% $H_2O_2$).

Such oxidizing agent preparations are preferably aqueous, flowable oxidizing agent preparations. Here, preferred preparations are exemplified in that the flowable oxidizing agent preparation—in relation to its weight—contains from about 40 to about 90% by weight, preferably from about 50 to about 85% by weight, particularly preferably from about 55 to about 85% by weight, more preferably from about 60 to about 85% by weight, and in particular from about 70 to about 85% by weight of water.

It has also proven to be advantageous if the oxidizing agent preparation (B) contains at least one stabiliser or complexing agent. Conventional complexing agents and stabilisers that are also preferred within the scope of the present disclosure are, for example polyoxycarboxylic acids, polyamines, ethylenediaminetetraacetic acid (EDTA), N-hydroxyethylethylenediaminetriacetic acid, diethylenetriaminepentaacetic acid (DTPA), ethylenediaminedisuccinic acid (EDDS), hydroxyethyliminodiacetic acid, nitridodiacetic acid-3-propionic acid, isoserindiacetic acid, N,N-di-(2-hydroxyethyl)glycine, N-(1,2-dicarboxy-2-hydroxyethyl)glycine, N-(1,2-dicarboxy-2-hydroxyethyl)aspartic acid or nitrilotriacetic acid (NTA), ethylenediaminediglutaric acid (EDGA), 2-hydroxypropylendiamindisuccinc acid (HPDS), glycinamide-N,N'-disuccinic acid (GADS), ethylenediamine-N—N'-diglutaric acid (EDDG), 2-hydroxypropylenediamine-N—N'-disuccinic acid (HPDDS), diaminoalkyldi-(sulfosuccinic acid) (DDS), ethylenedicysteic acid (EDC), ethylenediamine-N—N'-bis(ortho-hydroxyphenyl) acetic acid (EDDHA), N-2-hydroxyethylamine-N,N-diacetic acid, glyceryliminodiacetic acid, iminodiacetic acid-N-2-hydroxypropylsulfonic acid, aspartic acid-N-carboxymethyl-N-2,5-hydroxypropyl-3-sulfonic acid,β-alanine-N,N'-diacetic acid, aspartic acid-N,N'-diacetic acid, aspartic acid-N-monoacetic acid, dipicolinic acid, and colour-changing salts and/or derivatives thereof, geminal diphosphonic acids such as 1-hydroxyethan-1,1-diphosphonic acid (HEDP), higher homologues thereof with up to 8 carbon atoms and hydroxy or amino group-containing derivatives hereof and 1-aminoethan-1,1-diphosphonic acid higher homologues thereof with up to 8 carbon atoms and hydroxy or amino group-containing derivatives, aminophosphonic acids such as ethylenediaminetetra(methylenephosphonic acid) (EDTMP), diethylene-triaminepenta(methylenephosphonic acid) (DTPMP) and higher homologues thereof, or nitrilotri(methylenephosphonic acid), phosphonopolycarboxylic acids such as 2-phosphonobutan-1,2,4-tricarboxylic acid, cyclodextrins, and alkalistannates (sodium stannate), alkalipyrophosphates (tetrasodiumpyrophosphate, disodiumpyrophosphate), alkaliphosphates (sodiumphosphate), and phosphoric acid and colour-changing salts thereof.

Further Ingredients

The agents as contemplated herein forming the first and second subject of the present disclosure and/or the oxidizing agent preparation (B) of the kit-of-parts as contemplated herein can additionally contain further active substances, auxiliaries and additives, which are different from the previously described constituents (a) to (f). These can be, for example: cationic surfactants, amphoteric surfactants, anionic surfactants, non-ionic surfactants (which are different from the constituents (a( ) to (d)), anionic, non-ionic and/or cationic polymers, structuring agents such as glucose, maleic acid and lactic acid, perfume oils, fibre structure-improving active substances, in particular mono-, di- and oligosaccharides, such as glucose, galactose, fructose, fruit sugars and lactose; colorants for coloring the agent; anti-dandruff active substances, such as piroctone, olamine, zinc omadine and climbazole; amino acids and oligopeptides; animal-based and/or plant-based protein hydrolysates, and those in the form of their fatty acid condensation products or optionally anionically or cationically modified derivatives; vegetable oils; light stabilisers and UV blockers; active substances such as panthenol, pantothenic acid, pantolactone, allantoin, pyrrolidinone carboxylic acids and colour-changing salts thereof and bisabolol; polyphenols, in particular hydroxycinnamic acids, 6,7-dihydroxycoumarin, hydroxybenzoic acids, catechins, tannins, leukoanthocyanidins, anthocyanidins, flavanones, flavones and flavonols; ceramides or pseudoceramides; vitamins, pro-vitamins and vitamin precursors; plant extracts; swelling and penetrating substances such as glycerol, propylene glycol monoethyl ether, carbonates, hydrogen carbonates, guanidines, ureas and primary, secondary and tertiary phosphates; turbidity agents such as latex, styrene/PVP and styrene/acrylamide copolymers; pearlescent agents such as ethylene glycol mono- and distearate and PEG-3 distearate; pigments as well as propellants such as propane-butane mixtures, $N_2O$, dimethyl ether, $CO_2$ and air.

The additional active substances ad auxiliaries are used in the agents as contemplated herein preferably in amounts of, in each case, from about 0.001 to about 10% by weight, in particular from about 0.0005 to about 5% by weight, in relation to the total weight of the agent (A) or the oxidizing agent preparation (B).

That said in respect of the preferred embodiments of the multi-component packaged unit applies mutatis mutandis in respect of the agents as contemplated herein.

Method

A fourth subject of the present disclosure is a method for producing an agent for dyeing keratin fibers, in particular human hair, comprising the following steps
(a) providing a cosmetic base formulation
(b) incorporating one or more oxidation dye precursors in salt form (A) into the base formulation,
(c) incorporating one or more water-soluble salts of barium and/or of calcium (B) into the base formulation,
wherein the molar ratio of all oxidation dye precursors in salt form (A) used in the base formulation to all water-soluble barium and calcium salts (B) used in the base formulation, i.e. the molar ratio (A)/(B), lies at a value of from about 1.0 to about 1.4.

That said in respect of the preferred embodiments of the method as contemplated herein applies mutatis mutandis in respect of the agent as contemplated herein.

EXAMPLES

1. Formulations

The following compositions were produced (unless stated otherwise, all values are in % by weight)

|  | V1 Comparison | V2 Comparison | E Invention |
|---|---|---|---|
| $C_{16}$-$C_{16}$ fatty alcohols | 12.00 | 12.00 | 12.00 |
| $C_{12}$-$C_{18}$ fatty alcohols | 2.40 | 2.40 | 2.40 |
| Ceteareth-20 | 0.90 | 0.90 | 0.90 |
| Cocoamidopropylbetaine | 0.12 | 0.12 | 0.12 |
| Ceteareth-50 | 1.50 | 1.50 | 1.50 |
| Potassium hydroxide | 0.5 | 0.5 | 0.5 |
| Monoethanolamine | 5.50 | 5.50 | 5.50 |
| Etidronic acid (60% aqueous solution) | 0.20 | 0.20 | 0.20 |
| Sodium sulfite | 0.40 | 0.40 | 0.40 |
| p-toluene diamine, sulfate (220.25 g/mol) | 1.80 | 3.26 | 3.26 |
| 1,5-dihydroxynaphthalene | 0.04 | 0.04 | 0.04 |
| Resorcinol | 0.40 | 0.50 | 0.50 |
| 4-chlororesorcinol | 0.45 | 0.68 | 0.68 |
| 5-amino-2-methylphenol | 0.035 | 0.035 | 0.035 |
| 3-amino-2-methylamino-6-methoxypyridine | 0.078 | 0.60 | 0.60 |
| Vitamin C | 0.2 | 0.2 | 0.2 |
| Sodium silicate 40/42 | 0.5 | 0.5 | 0.5 |
| Water | ad 100 | ad 100 | ad 100 |
| Barium hydroxide $(Ba(OH)_2$ 171.34 g/mol) | — | — | 2.1 (12.25 mmol) |
| Oxidation dye precursors in salt form (A) (millimol) | 8.17 mmol | 14.8 mmol | 14.8 mmol |
| Molar ratio (A)/(B) | — | — | 1.21 |

Each coloring cream of Examples 1 to 3 was mixed in a ratio of 1:1 with the following oxidizing agent preparation:

| Oxidizing agent preparation | OX |
|---|---|
| Dipicolinic acid | 0.1 g |
| Sodium pyrophosphate | 0.03 g |
| Etidronic acid (60% aqueous solution) | 1.50 g |
| Sodium laureth sulfate | 0.53 |

-continued

| Oxidizing agent preparation | OX |
|---|---|
| Acrysol 22 | 0.60 g |
| Hydrogen peroxide (50% aqueous solution) | 6.0 g |
| Sodium hydroxide (45% aqueous solution) | 0.80 g |
| Water (dist.) | ad 100 a |

2. Viscosities

The viscosities both of the coloring creams and of the application mixtures were measured

| | Viscosities of the coloring creams | | |
|---|---|---|---|
| | V1 | V2 | E Invention |
| p-toluene diamine, sulfate (220.25 g/mol) | 1.80 | 3.26 | 3.26 |
| Barium hydroxide (Ba(OH)$_2$ (171.34 g/mol) | — | — | 2.1 (12.25 mmol) |
| Oxidation dye precursors in salt form (A) (Millimol) | 8.17 mmol | 14.8 mmol | 14.8 mmol |
| Molar ratio (A)/(B) | — | — | 1.21 |
| Viscosity (20° C./Haake Rheostress 6000/measured with cone 35/1 geometry, diameter 35 mm and 1° angle/shear rate 7.2 s$^{-1}$) | 22557 mPas | 11000 mPas | 24310 mPas |

| | Viscosities of the application mixture | | |
|---|---|---|---|
| | V1 + OX | V2 + OX | E + OX Invention |
| p-toluene diamine, sulfate (220.25 g/mol) | 1.80 | 3.26 | 3.26 |
| Barium hydroxide (Ba(OH)$_2$ (171.34 g/mol) | — | — | 2.1 (12.25 mmol) |
| Oxidation dye precursors in salt form (A) (millimol) | 8.17 mmol | 14.8 mmol | 14.8 mmol |
| Molar ratio (A)/(B) | — | — | 1.21 |
| Viscosity (20° C./Haake Rheostress 6000/measured with cone 35/1 geometry, diameter 35 mm and 1° angle/shear rate 7.2 s$^{-1}$) | 12920 mPas | 5830 mPas | 7979 mPas |

3. Storage Test

Coloring creams V2 and E (both with a content of p-toluene diamine sulfate of 3.26% by weight) were stored in a temperature-controlled cabinet for 8 weeks at 40° C. After this time, the state of the formulations was assessed visually.

| | V2 | E Invention |
|---|---|---|
| 40° C., 8 weeks | Phase separation into fat phase and water phase | stable emulsion |

While at least one exemplary embodiment has been presented in the foregoing detailed description, it should be appreciated that a vast number of variations exist. It should also be appreciated that the exemplary embodiment or exemplary embodiments are only examples, and are not intended to limit the scope, applicability, or configuration of the various embodiments in any way. Rather, the foregoing detailed description will provide those skilled in the art with a convenient road map for implementing an exemplary embodiment as contemplated herein. It being understood that various changes may be made in the function and arrangement of elements described in an exemplary embodiment without departing from the scope of the various embodiments as set forth in the appended claims.

The invention claimed is:

1. An agent for dyeing keratin fibers wherein it is produced by mixing:
   (A) one or more oxidation dye precursors in salt form, and
   (B) one or more water-soluble salts of barium and/or of calcium,
   wherein the molar ratio of all oxidation dye precursors in salt form (A) used in the agent to all water-soluble barium and calcium salts (B) used in the agent is from about 1.0 to about 1.4, and
   wherein the one or more water-soluble salts of barium and/or of calcium is selected from the group of barium hydroxide, calcium hydroxide, and a combination thereof.

2. The agent according to claim 1, wherein it is produced by mixing (A) one or more oxidation dye precursors in salt form in the form of their polyvalent salts.

3. The agent according to claim 1, wherein it is produced by mixing (A) one or more oxidation dye precursors from the group of phenylenediamine sulfate, 2-(2-hydroxyethyl)-p-phenylenediamine sulfate, N,N-bis-(2-hydroxyethyl)-p-phenylenediamine sulfate, 2-methoxymethyl-p-phenylenediamine sulfate, 2,4,5,6-tetraaminopyrimidine monosulfate, 2,4,5,6-tetraaminopyrimidine disulfate, 4,5-diamino-1-(2-hydroxyethyl)-1H-pyrazole sulfate, or combinations thereof.

4. The agent according to claim 1, wherein the total amount of all oxidation dye precursors in salt form (A) used in the agent, in relation to the total weight of the agent, is from about 0.1 to about 6.5% by weight.

5. The agent according to claim 1, wherein the molar ratio of all oxidation dye precursors in salt form (A) used in the agent to all water-soluble barium and calcium salts (B) used in the agent is from about 1.0 to about 1.35.

6. The agent according to claim 1, wherein the agent is present in the form of an oil-in-water emulsion.

7. The agent according to claim 1, wherein the agent is utilized in a multi-component packaged unit for the oxidative dyeing of keratin fibers comprising, packaged separately from one another,
   a first container comprising a cosmetic agent (I), and
   a second container comprising a cosmetic agent (II),
   wherein
   the agent (I) in the first container is a dye according to claim 1, and
   the agent (II) in the second container is an oxidizing agent preparation comprising hydrogen peroxide.

8. A method for producing an agent for dyeing keratin fibers, comprising the following steps:
   (a) providing a cosmetic base formulation,
   (b) incorporating one or more oxidation dye precursors in salt form (A) into the base formulation, and
   (c) incorporating one or more water-soluble salts of barium and/or of calcium (B) into the base formulation,
   wherein the molar ratio of all oxidation dye precursors in salt form (A) used in the base formulation to all water-soluble barium and calcium salts (B) used in the base formulation is from about 1.0 to about 1.4, and
   wherein the one or more water-soluble salts of barium and/or of calcium (B) is selected from the group of barium hydroxide, calcium hydroxide, and a combination thereof.

9. The agent according to claim 1, wherein the one or more water-soluble salts of barium and/or of calcium comprises barium hydroxide.

10. The agent according to claim 1, wherein one or more oxidation dye precursors in salt form comprises p-toluene diamine sulfate.

11. The agent according to claim 1, wherein the agent comprising one or more oxidation dye precursors in salt form (A) and one or more water-soluble salts of barium and/or of calcium (B) exhibits improved storage stability after storage for 8 weeks at 40° C. as compared to an agent comprising one or more oxidation dye precursors in salt form (A) and free of water-soluble salts of barium and/or of calcium (B).

12. An agent for dyeing keratin fibers wherein it is produced by mixing:
 (A) one or more oxidation dye precursors in salt form, and
 (B) one or more water-soluble salts of barium and/or of calcium,
 wherein the molar ratio of all oxidation dye precursors in salt form (A) used in the agent to all water-soluble barium and calcium salts (B) used in the agent is from about 1.0 to about 1.4, wherein the agent comprises or is produced by mixing:
 (A) p-toluene diamine sulfate, and
 (B) barium hydroxide,
 wherein the molar ratio of p-toluene diamine sulfate (A) used in the agent to barium hydroxide (B) used in the agent is from about 1.0 to about 1.4.

13. The agent according to claim 12, wherein the agent comprising p-toluene diamine sulfate (A) and barium hydroxide (B) exhibits improved storage stability after storage for 8 weeks at 40° C. as compared to an agent comprising p-toluene diamine sulfate (A) and free of barium hydroxide (B).

14. The agent according to claim 1, wherein the agent comprises:
 (A') p-toluene diamine sulfate, and
 (B') barium hydroxide,
 wherein the molar ratio of p-toluene diamine (A') used in the agent to barium hydroxide (B') used in the agent is from about 1.0 to about 1.4.

15. The agent according to claim 14, wherein the agent comprising p-toluene diamine sulfate (A) and barium hydroxide (B) exhibits improved storage stability after storage for 8 weeks at 40° C. as compared to an agent comprising p-toluene diamine sulfate (A) and free of barium hydroxide (B).

* * * * *